US006501548B1

(12) United States Patent
Oldenbourg (10) Patent No.: US 6,501,548 B1
(45) Date of Patent: Dec. 31, 2002

(54) RETARDANCE MEASUREMENT METHOD

(75) Inventor: Rudolf Oldenbourg, Falmouth, MA (US)

(73) Assignee: Cambridge Research & Instrumentation Inc., Woburn, MA (US)

( * ) Notice: Subject to any disclaimer, the term of this patent is extended or adjusted under 35 U.S.C. 154(b) by 0 days.

(21) Appl. No.: 09/883,602

(22) Filed: Jun. 18, 2001

Related U.S. Application Data
(60) Provisional application No. 60/212,173, filed on Jun. 16, 2000.

(51) Int. Cl.[7] .................................................. G01J 4/00
(52) U.S. Cl. ........................ 356/368; 356/366; 356/367
(58) Field of Search .......................... 359/371; 356/364, 356/366, 367, 368

(56) References Cited

U.S. PATENT DOCUMENTS 5,521,705 A 5/1996 Oldenbourg et al. ........ 356/368
6,320,657 B1 * 11/2001 Aspnes et al. .............. 356/369

* cited by examiner

*Primary Examiner*—Georgia Epps
*Assistant Examiner*—David N. Spector
(74) *Attorney, Agent, or Firm*—Cohen, Pontani, Lieberman & Pavane (57) ABSTRACT

A method for measuring sample retardance in the presence of spurious background retardance contributed by optical components such as strained lenses in the measurement system, which is accurate where there is a retardance in excess of 15 degrees in the sample, the background, or the combination thereof. The method can be applied to imaging systems that record polarized light intensities for obtaining retardance magnitude and angular orientation values at all points in a scene simultaneously. The system first takes images that record the apparent slow axis orientation and the apparent retardance of the sample at all image points. Then the sample is removed and images are taken that record the background retardance alone. Algorithms for minimizing the effect of the background retardance on the measured sample retardance make use of the separately measured polarized light intensities of sample with background and of the background alone. The algorithms can be applied to each picture element simultaneously and do not make use of spatial relationships or distributions within the sample.

17 Claims, 4 Drawing Sheets

Prior Art

Fig. 1

(Prior Art)

RETARDANCE MEASUREMENT METHOD

This application claims the benefit of provisional application No. 60/212,173, filed Jun. 16, 2000.

BACKGROUND OF THE INVENTION

1. Field of the Invention

The invention is directed toward systems for measuring materials properties such as strain, crystallinity, thickness, purity, composition, and the like of samples; or for observing structures in transparent materials; or, for measurement of strain in models constructed for that purpose. It is more narrowly directed toward measuring systems that utilize polarized light for such measurements. It may be used in applications including scientific research, industrial measurement, quality control, forensics, and medical imaging.

2. Description of the Related Art

Polarization interference is a well-known way to observe birefringence or retardance in a sample. Birefringence is an intensive property of a sample whereby light polarized along different axes will experience different indices of refraction. The axis along which the index is lowest is termed the fast axis, and that along which the index is highest is termed the slow axis; these are necessarily perpendicular to one another. The optical indices are termed $n_f$ and $n_s$. Retardance R is an extensive quantity measuring the optical path difference experienced by polarized light when passing through a sample. For a uniform sample at normal incidence $R=(n_s-n_f) * d$, where d is the thickness of the sample.

There is a large literature describing apparatus and methods for determining the retardance of a sample. These use some form of polarized light that is either transmitted through or reflected by the sample. The change in polarization upon transmission or reflection is measured in order to determine the sample retardance. In many cases the apparatus include other optical components such as lenses that distort the polarization of light. Such polarization distortions superimpose as spurious background retardance and modify the measured sample retardance. There is a need for a method that minimizes the effect of background retardance. This is especially so for imaging systems that measure the retardance at a multitude of sample points simultaneously. In imaging systems polarization distortions typically vary from image point to image point and there are no optical methods known that can effectively compensate for the multitude of background retardance values.

Oldenbourg and Mei U.S. Pat. No. 5,521,705 teaches how to unambiguously identify the slow axis and value of R for a birefringent sample. This method uses an imaging detector and variable retarders to determine the retardance at an array of sample points. Equations for calculating retardance are given, which provide a good approximation when the retardance is less than $\frac{1}{25}^{th}$ of the wavelength. Oldenbourg and Mei also show that the background retardance can successfully be separated and removed from images of samples, where the samples have small retardance magnitude values ($\leq \lambda/25$). For larger phase angles ($\lambda/24$ or 15 degrees) the equations are not sufficiently accurate.

SUMMARY OF THE INVENTION

It is a goal of the present invention to obtain images of retardance R in a sample in the presence of so-called background retardance that is contributed by other components than the sample in the measuring system. By background retardance we refer to any property of optical components that alter the polarization of transmitted or reflected light, including without limitation stress birefringence and birefringent inclusions in glass, or the differential reflection or transmission of s- and p-polarized light at dielectric interfaces. It is a particular goal of the present invention to describe a background correction procedure that can be applied to larger sample retardance values ($\geq 2\lambda/24$) of up to $\lambda/2$ and beyond, as well as to smaller values.

The invention is based on the recognition that, when measuring the retardance of a sample, the result is modified by the presence of contaminating background retardance. The measuring system usually measures a combination of the sample retardance and the apparent background retardance. We call this combination the measured sample retardance. After moving the sample out of the light path of the measuring system, the background retardance contributed by all optical elements other than the sample is determined separately. A goal of the present invention is to use the data set of the background retardance to remove it from the data set of the measured sample retardance in order to determine a more accurate value of the sample retardance, i.e. its magnitude and slow axis orientation. Since the retardance is a vector quantity, this removal is not a purely arithmetic operation.

The invention describes measurement and data analysis procedures that were developed based on the measuring system of Oldenbourg. This system employs monochromatic light with a single center wavelength. The instrument can unambiguously measure sample retardance up to half wavelength. The direction of the slow axis of the background and the sample retardance can be aligned to any direction in the image plane.

In the case that the sample retardance is larger than half wavelength, a measuring system that employs more than one center wavelength is needed to unambiguously measure sample retardance. The current invention can be applied to such systems if the multi-wavelength measurement process is performed as a sequence of single wavelength measurements, as described in the pending U.S. application Ser. No. 09/595,827 entitled "Polarization Imaging System" by Clifford Hoyt, filed Jun. 16, 2000, the entire contents of which are incorporated herein by reference.

The current invention is especially useful for imaging systems that provide an array of measurements that display the spatial distribution of sample retardance. Typically, the background retardance contributed to the sample retardance changes from point to point in the image. It is a goal of the current invention to account for this variation and correct each image point with the appropriate background retardance.

Other aspects of the invention will be apparent from the Figures and description of the preferred embodiment, which are now presented.

DETAILED DESCRIPTION OF THE PRESENTLY PREFERRED EMBODIMENTS

Throughout this text, certain embodiments quantify retardance in terms of an apparent phase angle, expressed in radians or degrees; while others describe it in terms of a physical distance, such as a certain number of nanometers (nm). This is done to illustrate that either approach is possible, and that indeed the two are equivalent.

The design of a polarization imaging instrument, termed the pol-scope, is described more fully in U.S. Pat. No. 5,521,705, the entire contents of which are incorporated herein by reference. The preferred embodiment of the current invention uses an optical system such as the pol-scope for obtaining images of retardance magnitude R and azimuth or fast axis orientation ρ at a multitude of sample points. But use of this particular optical system is not critical, and one may employ any optical system that provides equivalent information on R and ρ, either for a single point at a time, or for all points in an image at once, without deviating from the spirit of the present invention.

The present invention is based on the recognition that the measured retardance is a combination of the sample retardance [$R_{sample}$, $\rho_{sample}$] and an apparent background retardance [$R_{Bg}$, $\rho_{Bg}$] contributed by the optical components of the instrument.

It is a goal of the present invention to present efficient and accurate data acquisition and analysis methods to determine a more accurate sample retardance by removing the background retardance from the measured sample retardance.

Figure 1:
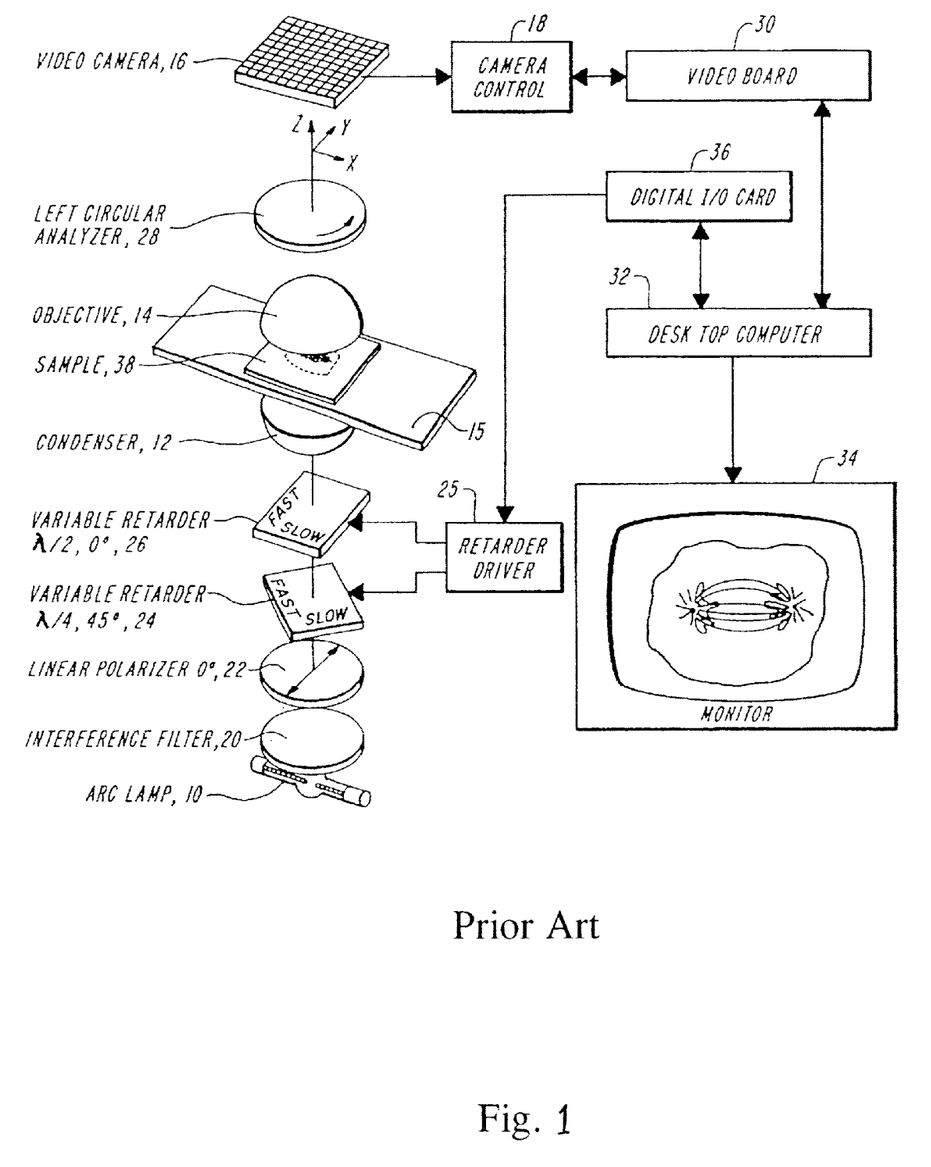
FIG. 1 shows a first embodiment of the retardance measurement system where the universal compensator is placed in the illumination path of the instrument.

FIG. 1 illustrates the pol-scope system as implemented in an optical microscope stand. As is conventional, the microscope itself includes a lamp 10 such as a mercury arc or other type; and a condenser lens 12 and an objective lens 14, such as a 60×1.4-NA Plan APO objective lens, on opposite sides of a sample stage 15. The light from a sample on the sample stage is directed to a video camera and imaged at its CCD detector array.

Further, the light path between the lamp 10 and video camera 16 also includes, on the illumination side of the condenser lens 12, an interference filter 20, a linear polarizer 22 (mounted with its transmission axis oriented at 0° to a reference axis), and a pair of variable, liquid crystal, electro-optical retarders 24, 26 with their principal slow axes positioned, respectively, at 45° and 0° to the reference axis. In the optical path on the imaging side of the sample stage 15 and objective lens 14, i.e., between the objective lens and the video camera 16, is a left circular analyzer 28. In the disclosed preferred embodiments, the variable retarders/electro-optic modulators are liquid crystal devices obtained from Cambridge Research and Instrumentation, Inc. (Woburn, Mass.). In other implementations of the pol-scope system, different types of variable retarders or electro-optic modulators, such as Pockels cells, Kerr cells, PLZT plates, or the like, may also be used. Similarly, other light sources, e.g., incandescent lamps or lasers, may be used in place of mercury vapor lamps; monochromators or the like may be used in lieu of an interference filter; and a photodiode, photodiode array, charge-injection device (CID), CMOS detector, bolometric imager, pyroelectric sensor, or other photodetector may be used in lieu of the CCD video camera and associated optics of the preferred embodiments.

It will be appreciated that, in the illustrated pol-scope of FIG. 1, the two variable retarders 24, 26 are located in the illumination path between linear polarizer 22 and the condenser lens 12. In a traditional polarizing microscope this is a possible location for the traditional compensator. Therefore, the combination of two variable retarders 24, 26 is called a universal compensator, for reasons that will become apparent later. In another implementation, the variable retarders may be placed in the imaging path (as shown in FIG. 2) as can be done with the compensator in a traditional polarizing microscope.

Figure 2:
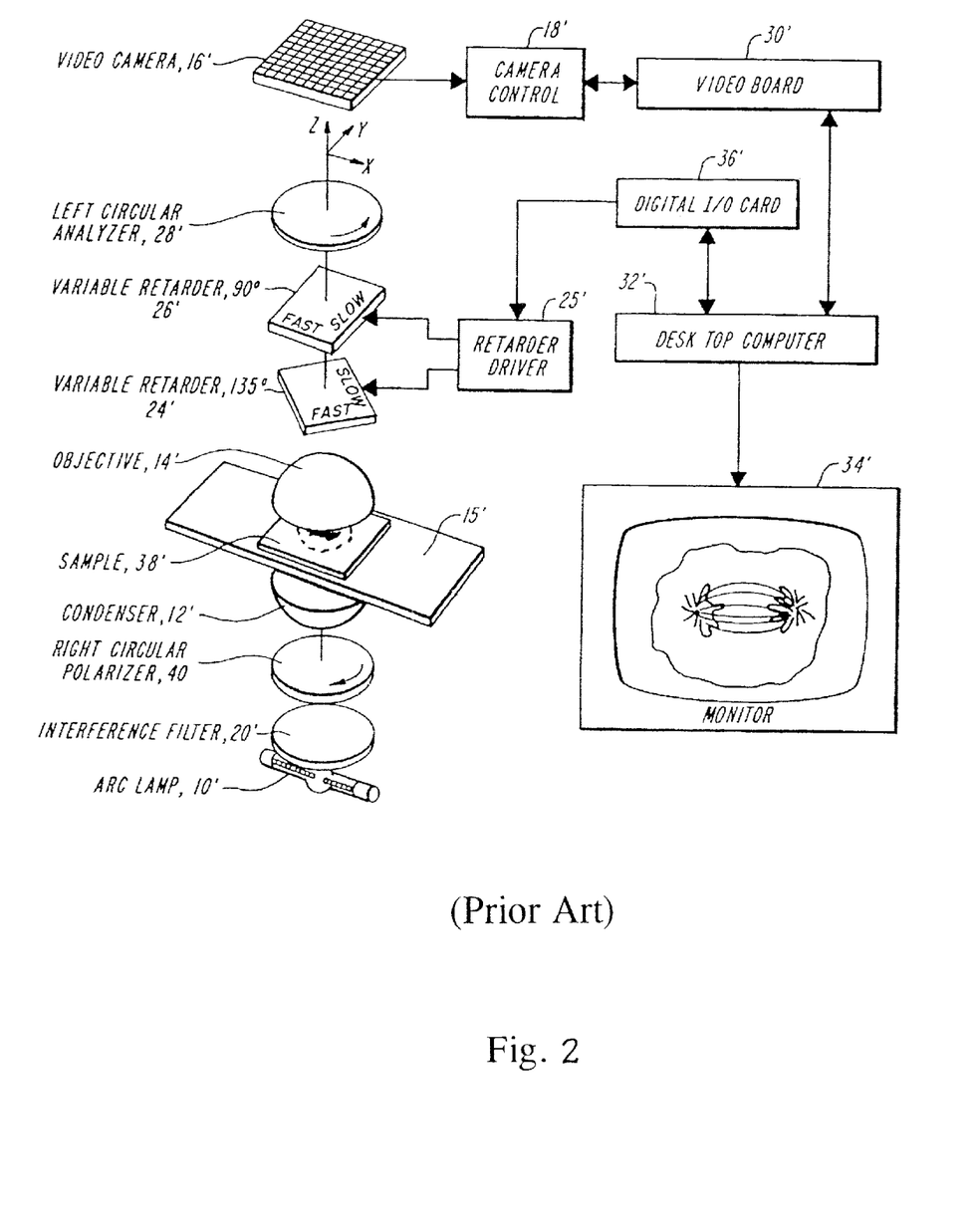
FIG. 2 shows another embodiment of the retardance measurement system where the universal compensator is placed in the imaging path of the instrument

It will also be appreciated that systems shown in FIGS. 1 and 2 herein employ transmission microscopes in which the illuminating and imaging paths are on opposite sides of the specimen stage.

The pol-scope can also be implemented as an epi-illumination microscope in which the illuminating and imaging paths are on the same side of the specimen stage for measurement of reflective samples. In such epi-illumination microscopes, a single objective lens can serve both as a condenser to illuminate the specimen and as an objective to collect the back-scattered light from the specimen and project an image on the video cameras. In these embodiments, a beam splitter, known to be specially designed for reflective polarized light microscopes to minimize polarization aberrations, is placed on the side of the objective away from the specimen (i.e., the objective lens is between the beam splitter and the specimen) to separate the illumination path from the imaging path.

As illustrated in connection with the transmission microscope systems of FIGS. 1 and 2, a pair of variable retarders, a polarizing analyzer, and (depending on the particular implementation) one or more other polarizing elements, are placed in the illumination and imaging paths. Retarders, analyzers and other polarizing elements of equivalent type are positioned in equivalent positions in the illumination and imaging paths of reflective polarized light microscope systems. Further, the operation of epi-illumination microscope systems for measuring polarized light and specimen optical properties is essentially the same as described hereinafter with respect to the transmission systems of FIGS. 1 and 2, which employ transmission-type microscopes to measure polarized light and specimen optical properties.

The optical arrangement shown in FIG. 1 is sensitive to the magnitude of the birefringence of specimen 38, and to the orientation of the fast and slow axes of the specimen. Hence the images recorded by camera 16 will reflect the distribution of specimen retardance/birefringence (i.e., the birefringence in the portion of the specimen corresponding to each element of the detector array of the camera) in magnitude and orientation. It will, of course, be recognized that birefringence and retardance are related, and the two terms are often used interchangeably. Birefringence δn is an optical property of a specimen, and retardance R characterizes the change in polarization of light passing through the specimen. The two are related by:

$$R = \delta nd \quad [1]$$

where d is the specimen thickness.

Figure 3:
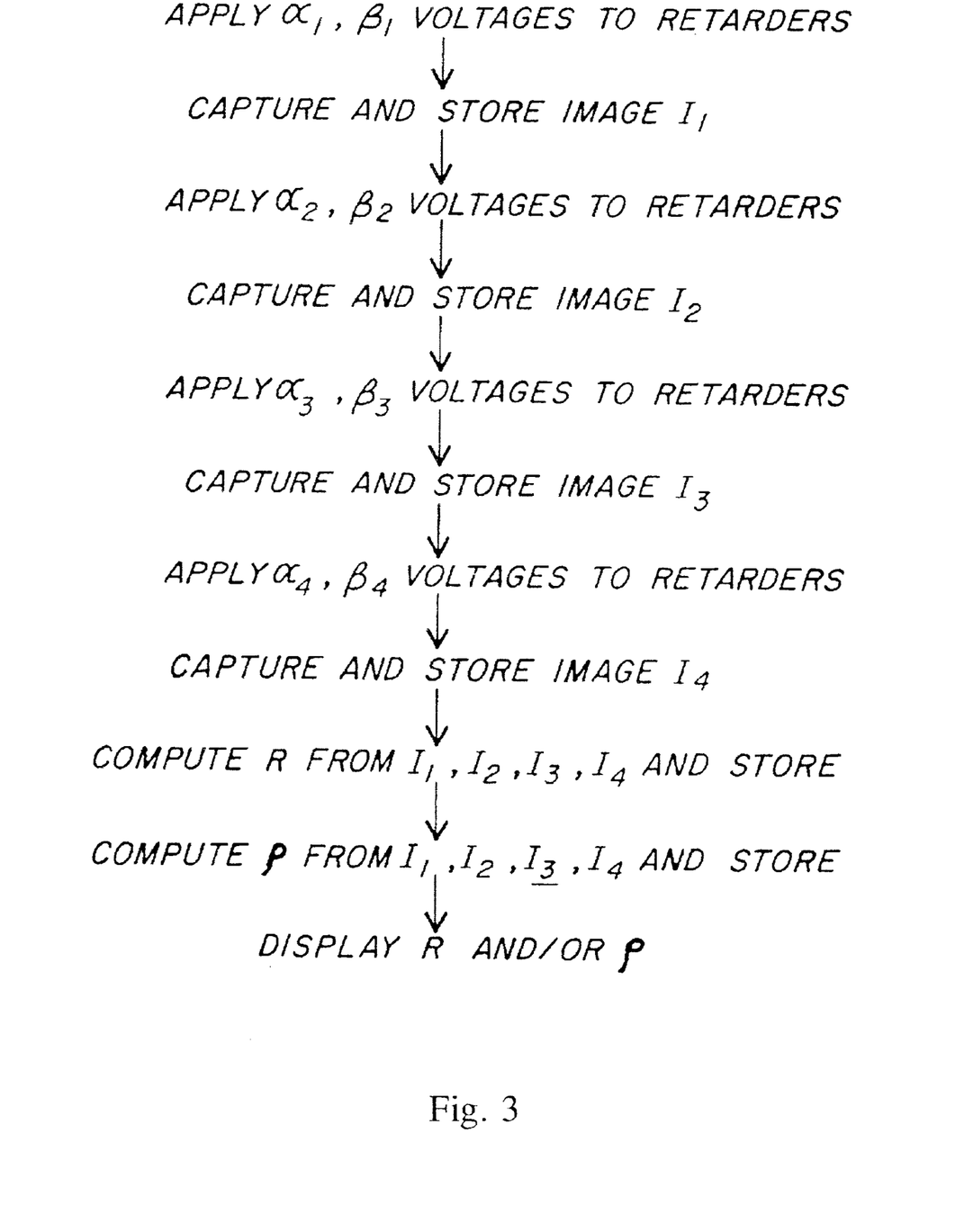
FIG. 3 is a simplified flow-chart illustrating a sequence of operation of the retardance measurement system.
Figure 4A:
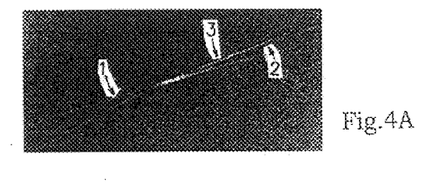
FIGS. 4a–4f show an illustration of background correction procedure on retardance and azimuth images of microtubules (single microtubules are 25 nm thick, several microns long, stiff and weakly birefringent biopolymers). Microtubules grow off the ends of a short piece of axoneme, a birefringent rod-shaped polymerization seed (near image center) which is stuck to the microscope coverglass. The specimen images in the top row (FIG. 4a: retardance image, FIG. 4b: azimuth image) are noticeably affected by background retardance. The center row (FIGS. 4c and 4d) shows images of the background alone recorded after the preparation was moved sideways to a clear specimen area. The bottom row (FIGS. 4e and 4f) shows the same specimen images as in the top row after the background correction procedure was applied. The background corrected specimen images show a uniform background with noise due to uncertainties in measured intensities. The corrected retardance of microtubule bundles, containing one or more microtubules growing off the ends of axonemes, was measured to be in the range of 0.07 to 0.2 nm.
Figure 4B:
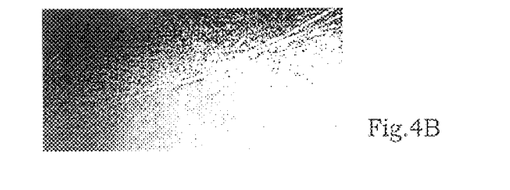
Figure 4C:
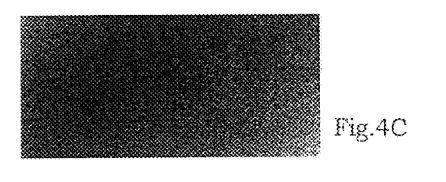
Figure 4D:
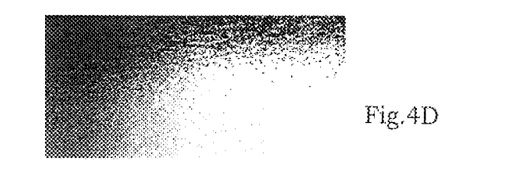
Figure 4E:
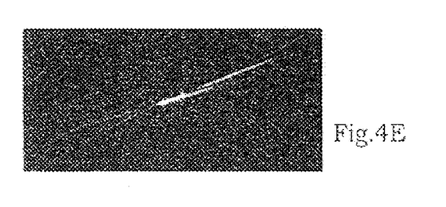
Figure 4F:
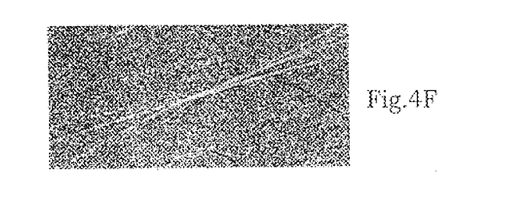

The operational sequence of the systems of FIGS. 1 and 2, under the control of the computer 32, 32', is generally as shown in FIG. 3. Thus, the intensity of the light passing analyzer 28, 28' is measured at a plurality of predetermined settings of the variable retarders. Typically, four intensity measurements are made. The retardance (magnitude and/or orientation) of the specimen is determined based on the measured (typically four) light intensities, and the known retardance values of the variable retarders corresponding to each intensity measurement. One light intensity image is taken with the variable retarders at their initial settings, and the three other intensity images are taken with the retarders at different, predetermined and mutually independent retarder settings. The differences in retardance between the initial setting and the other predetermined retarder settings are typically chosen to be about the same magnitude as the maximum retardance expected to be measured in the specimen.

For each region of the specimen in the field of camera view (e.g., for each region light from which is incident on a detector of the detector array, or for each region corresponding to a pixel of the display), the specimen region anisotropy is produced and displayed (or otherwise recorded or output) based on the intensity of the four images corresponding to that region.

Table 1 lists retarder settings and recorded intensities for the preferred embodiment of the present invention. Intensity values are stored in the computer 32 as 2-dimensional image arrays and all further manipulation is done with the computer. The retarder settings are expressed as fractions of the wavelength λ of the illuminating light. The term "swing" represents a selected retardance value which is typically of the same magnitude as the sample retardance expected to be measured in the specimen.

TABLE 1

| Intensity | retarder 24 | retarder 26 |
|---|---|---|
| $I_1$ | λ/4 | λ/2 |
| $I_2$ | λ/4 + swing | λ/2 |
| $I_3$ | λ/4 | λ/2 + swing |
| $I_4$ | λ/4 | λ/2 − swing |

For convenience the following intermediate results are formed:

$$term1 = I_3 + I_4 - 2 \cdot I_1 \quad [2a]$$

$$term2 = I_3 - I_4 \quad [2b]$$

$$term3 = I_3 + I_4 - 2 \cdot I_2 \quad [2c]$$

Using these terms the expression for the measured retardance magnitude magn, expressed as a phase angle between 0° (0) and 180° (λ/2), is as:

$$magn = \arctan\left(\tan\left(\frac{swing}{2}\right)\sqrt{\left(\frac{term2}{term1}\right)^2 + \left(\frac{term3}{term2}\right)^2}\right) \quad [3]$$

If term1 is negative, the retardance magnitude is 180° minus the above expression. If term1 is zero, the expressions $$\frac{term3}{term1} \text{ and } \frac{term2}{term1}$$

under the square root become infinity and the magnitude is 90°.

The expression for the "raw" azimuth is:

$$azim_{raw} = \frac{\arctan\left(\left|\frac{term3}{term2}\right|\right)}{2} \quad [4]$$

The raw azimuth is computed assuming only positive values for term2 and term3. Table 2 gives the actual azimuth values azim as a function of $azim_{raw}$ and the different sign combinations of the two terms.

TABLE 2

| term2 | term3 | azim |
|---|---|---|
| >0 | >0 | 180° − $azim_{raw}$ |
| >0 | ≤0 | $azim_{raw}$ |
| <0 | ≥0 | 90° + $azim_{raw}$ |
| <0 | <0 | 90° − $azim_{raw}$ |
| =0 | <0 | 45° |
| =0 | >0 | 135° |

The retardance magnitude and azimuth values that are computed with formulas [3] and [4] represent the measured retardance that is a combination of the sample retardance and the background retardance. The background retardance is due to polarization aberrations induced by components such as lenses and mirrors in the measurement system.

The background retardance can be measured separately by removing the specimen from the optical path and recording the background intensities $I_{1BG}$, $I_{2BG}$, $I_{3BG}$, and $I_{4BG}$ for the same retarder settings as shown in Table 1. Again, for convenience, intermediate terms are formed and used in expressions for the magnitude and azimuth of the background retardance:

$$term1Bg = I_{3BG} + I_{4BG} - 2 \cdot I_{1BG} \quad [5a]$$

$$term2Bg = I_3 - I_4 \quad [5b]$$

$$term3Bg = I_3 + I_4 - 2 \cdot I_2 \quad [5c]$$

$$magn_{BG} = \arctan\left(\tan\left(\frac{swing}{2}\right)\sqrt{\left(\frac{term2Bg}{term1Bg}\right)^2 + \left(\frac{term3Bg}{term1Bg}\right)^2}\right) \quad [6]$$

$$azim_{rawBG} = \frac{\arctan\left(\left|\frac{term3Bg}{term2Bg}\right|\right)}{2} \quad [7]$$

In analogy to expression [4], Table 2 gives the actual background azimuth values $azim_{BG}$ as a function of $azim_{raw}$ BG and the different sign combinations of the two terms $term2_{BG}$ and $term3_{BG}$.

The independent knowledge of the intensities $I_1$, $I_2$, $I_3$, and $I_4$ for the sample plus background retardance and the intensities $I_{1BG}$, $I_{2BG}$, $I_{3BG}$, and $I_{4BG}$ of the background retardance alone can be exploited to calculate a more accurate sample retardance. To this end, two different cases are distinguished:

Case 1: Both the sample retardance and the background retardance have small magnitude values, typically less than 15° phase angle.

Case 2: The magnitude of the sample retardance has a value anywhere between 0 and 180°, while the apparent background retardance remains small, i.e., less than 15 degrees.

In Case 1 the improved sample retardance is determined by the following replacements in Expressions [3] and [4]:

$$\frac{term2}{term1}$$

is replaced by $$\left(\frac{term2}{term1} - \frac{term2BG}{term1BG}\right);$$

and $$\frac{term3}{term1}$$

is replaced by $$\left(\frac{term3}{term1} - \frac{term3BG}{term1BG}\right),$$

leading to the following expressions $$magn_{case1} = \arctan\left(\tan\left(\frac{swing}{2}\right) * \sqrt{\left(\frac{term2}{term1} - \frac{term2BG}{term1BG}\right)^2 + \left(\frac{term3}{term1} - \frac{term3BG}{term1BG}\right)^2}\right) \quad [8]$$

$$azim_{raw,case1} = \frac{\arctan\left(\left|\frac{\left(\frac{term3}{term1} - \frac{term3BG}{term1BG}\right)}{\left(\frac{term2}{term1} - \frac{term2BG}{term1BG}\right)}\right|\right)}{2} \quad [9]$$

where Table 2 is used to determine the actual azimuth values $azim_{case\ 1}$, as a function of $azim_{rawcase1}$ and the different sign combinations of expressions $$\left(\frac{term3}{term1} - \frac{term3BG}{term1BG}\right) \text{ and } \left(\frac{term2}{term1} - \frac{term2BG}{term1BG}\right).$$

The result of correcting the measured sample retardance by such a replacement is shown in FIG. 4. As can be seen, the remaining systematic deviations in the calculated values of the sample retardance are generally smaller than the random fluctuations induced by uncertainties in measured light intensities.

In Case 2 the sample retardance can largely be restored except for some special circumstances. The first step in the background correction procedure is the same as in Case 1:

$$magn_{step1} = \arctan\left(\tan\left(\frac{swing}{2}\right) \cdot \sqrt{\left(\frac{term2}{term1} - \frac{term2BG}{term1BG}\right)^2 + \left(\frac{term3}{term1} - \frac{term3BG}{term1BG}\right)^2}\right) \quad [10]$$

$$azim_{raw,step1} = \frac{\arctan\left(\left|\frac{\left(\frac{term3}{term1} - \frac{term3BG}{term1BG}\right)}{\left(\frac{term2}{term1} - \frac{term2BG}{term1BG}\right)}\right|\right)}{2} \quad [11]$$

Table 2 is used to determine the actual azimuth values $azim_{step\ 1}$ as a function of $azim_{raw,\ step1}$ and the different sign combinations of expressions $$\left(\frac{term3}{term1} - \frac{term3BG}{term1BG}\right) \text{ and } \left(\frac{term2}{term1} - \frac{term2BG}{term1BG}\right).$$

In a second step, the magnitude of the sample retardance $magn_{case\ 2}$ is computed by applying a further correction, subtracting a fraction of the background retardance from the result obtained in step 1:

$$magn_{case\ 2} = magn_{step\ 1} - magn_{BG} \cdot \cos(2(azim_{step1} - azim_{BG})) \cdot [1 - \cos^2(magn_{step1})] \quad [12]$$

The azimuth value obtained in step 1 is not corrected any further:

$$azim_{case\ 2} = azim_{step\ 1} \quad [13]$$

For Case 2, said two-step correction is able to reduce systematic errors in the measured sample retardance to a similar degree as is reported for Case 1 and illustrated in FIG. 4. However, if the magnitude of the sample retardance is near 180° the two-step correction might fail. The failure only occurs for a sample retardance with magnitude in the range of (180°−$magn_{BG}$) to 180°. Under the following circumstances this failure can be avoided completely:

Circumstance 1: The background retardance is found in optical components that are exclusively located in the illumination path, for example in the condenser lens 12. Under this circumstance, the failure can be avoided by using an instrument set-up as shown in FIG. 1 in which the universal compensator 24,26 is placed in the illumination path between polarizer 22 and sample 38.

Circumstance 2: The background retardance is found in optical components that are exclusively located in the imaging path, for example in the objective lens 14. Under this circumstance, the failure can be avoided by using an instrument set-up as shown in FIG. 2 in which the universal compensator 24',26' is placed in the imaging path between sample 38' and analyzer 28'.

In general terms, the effectiveness of the background correction procedure can be improved by placing the universal compensator in the light path according to the location of the optical elements that introduce the largest polarization aberrations.

What is claimed is:

1. A method for measuring retardance in samples, said method comprising providing a source of monochromatic, polarized light having a wavelength $\lambda$;

providing a detector for detecting the intensity of light incident thereon, said detector and said source defining an optical path therebetween;

providing in said optical path a sample location for a sample whose retardance is to be measured, said sample having a retardance less than $\lambda/24$;

providing in said optical path a pair of variable light retarders positioned so that the slow optical axes thereof are at a 45 degree angle to each other;

measuring the light intensity at said detector for four different retarder settings with said sample in at said sample location, yielding light intensity values $I_1, I_2, I_3,$ and $I_4$;

measuring the light intensity at said detector for said four different retarder settings without said sample at said sample location, yielding light intensity values $I_{1BG}$, $I_{2BG}$, $I_{3BG}$; and $I_{4BG}$, determining a compensated retardance magnitude value for the sample corrected for background retardance directly from said measured light intensities with and without said sample at said sample location according to the equation $$magn_{case1} = \arctan\left(\tan\left(\frac{swing}{2}\right) * \sqrt{\left(\frac{term2}{term1} - \frac{term2BG}{term1BG}\right)^2 + \left(\frac{term3}{term1} - \frac{term3BG}{term1BG}\right)^2}\right)$$

wherein $term1=I_3+I_4-2I_1$, $term2=I_3-I_4$ $term3=I_3+I_4-2I_2$ $term1Bg=I_{4BG}+I_{4BG}-2I_{1BG}$ $term2Bg=I_{3BG}-I_{4BG}$ $term3Bg=I_{3BG}+I_{4BG}-2I_{2BG}$ and "swing" represents a selected retardance value which is typically the same magnitude as the retardance expected to be measured in the sample.

2. A method as in claim 1 wherein a raw azimuth value $azim_{raw}$ for said sample corrected for background retardance is determined according to the equation $$azim_{raw} = \frac{\arctan\left(\left|\frac{\left(\frac{term3}{term1} - \frac{term3BG}{term1BG}\right)}{\left(\frac{term2}{term1} - \frac{term2BG}{term1BG}\right)}\right|\right)}{2}$$

and an actual azimuth value is determined from the raw azimuth value and different sign combinations of expressions (term3/term1−term3BG/term1BG) and (term2/term1−term2BG/term1BG).

3. A method as in claim 2 wherein for (term2/term1−term2BG/term1BG)>0 and (term3/term1−term3BG/term1BG)>0, azim=180° −$azim_{raw}$.

4. A method as in claim 2 wherein for (term2/term1−term2BG/term1BG)>0 and (term3/term1−term3BG/term1BG)≦0, azim=$azim_{raw}$.

5. A method as in claim 2 wherein for (term2/term1−term2BG/term1BG)<0 and (term3/term1−term3BG/term1BG)≧0, azim=90° +$azim_{raw}$.

6. A method as in claim 2 wherein for (term2/term1−term2BG/term1BG)<0 and (term3/term1−term3BG/term1BG)<0, azim 90° −$azim_{raw}$.

7. A method as in claim 2 wherein for (term2/term1−term2BG/term1BG0) =0 and (term3/term1−term3BG/term1BG)<0, azim=45°.

8. A method as in claim 2 wherein for (term2/term1−term2BG/term1BG)=0 and (term3/term1−term3BG/term1BG)>0, azim=135°.

9. A method for measuring retardance in samples, said method comprising providing a source of monochromatic, polarized light having a wavelength $\lambda$;

providing a detector for detecting the intensity of light incident thereon, said detector and said source defining an optical path therebetween;

providing in said optical path a sample location for a sample whose retardance is to be measured, the sample having a retardance greater than $\lambda/24$;

providing in said optical path a pair of variable light retarders positioned so that the slow optical axes thereof are at a 45 degree angle to each other;

measuring the light intensity at said detector for four different retarder settings with said sample in at said sample location, yielding light intensity values $I_1, I_2, I_3,$ and $I_4$;

measuring the light intensity at said detector for said four different retarder settings without said sample at said sample location, yielding light intensity values $I_{1BG}$, $I_{2BG}$, $I_{3BG}$; and $I_{4BG}$, determining a compensated retardance magnitude value for the sample corrected for background retardance from said measured light intensities with and without said sample at said sample location.

10. A method as in claim 9 wherein a raw azimuth value for said sample corrected for background retardance is determined according to the equation $$azim_{raw} = \frac{\arctan\left(\left|\frac{\left[\frac{term3}{term1} - \frac{term3BG}{term1BG}\right]}{\left[\frac{term2}{term1} - \frac{term2BG}{term1BG}\right]}\right|\right)}{2}$$

wherein $term1=I_3+I_4-2I_1$ $term2=I_3-I_4$ $term3=I_3+I_4-2I_2$ $term1Bg=I_{4BG}+I_{4BG}-2I_{1BG}$ $term2Bg=I_{3BG}-I_{4BG}$ $term3Bg=I_{3BG}+I_{4BG}-2I_{2BG}$ and an actual azimuth value azim is determined from the raw azimuth value and different sign combinations of expressions (term3/term1−term3BG/term1BG) and (term2/term1−term2BG/term1BG).

11. A method as in claim 10 wherein for (term2/term1−term2BG/term1BG)>0 and (term3/term1−term3BG/term1BG)>0, azim=180°−$azim_{raw}$.

12. A method as in claim 10 wherein for (term2/term1−term2BG/term1BG)>0 and (term3/term1−term3BG/term1BG)≦0, azim=$azim_{raw}$.

13. A method as in claim 10 wherein for (term2/term1−term2BG/term1BG)<0 and (term3/term1−term3BG/term1BG)≧0, azim=$azim_{raw}$.

14. A method as in claim 10 wherein for (term2/term1−term2BG/term1BG)<0 and (term3/term1−term3BG/term1BG)<0, azim=$azim_{raw}$.

15. A method as in claim 10 wherein for (term2/term1−term2BG/term1BG) =0 and (term3/term1−term3BG/term1BG)<0, azim=45°.

16. A method as in claim 10 wherein for (term2/term1−term2BG/term1BG)=0 and (term3/term1−term3BG/term1BG)>0, azim 135°.

17. A method as in claim 10 wherein said compensated retardance magnitude value is determined according to the equation $$magn_2 = magn_{step\ 1} - magn_{BG} \cdot \cos(2(azim_{step1} - azim_{BG})) \cdot [1 - \cos^2(magn_{step})]$$

wherein $magn_{step1}=$ $$magn_{step1} = \arctan\left(\tan\left(\frac{swing}{2}\right) \cdot \sqrt{\left(\frac{term2}{term1} - \frac{term2BG}{term1BG}\right)^2 + \left(\frac{term3}{term1} - \frac{term3BG}{term1BG}\right)^2}\right)$$

wherein $magn_{BG}=$ $$magn_{BG} = \arctan\left(\tan\left(\frac{swing}{2}\right)\sqrt{\left(\frac{term2Bg}{term1Bg}\right)^2 + \left(\frac{term3Bg}{term1Bg}\right)^2}\right)$$

wherein $azim_{BG}$ is determined from $azim_{rawBG}$ and different sign combinations of expressions (term3/term1−term3BG/term1BG) and (term2/term1−term2BG/term1BG), and "swing" represents a selected retardance value which is typically the same magnitude as the retardance expected to be measured in the sample.

\* \* \* \* \*